(12) United States Patent
Dreyer

(10) Patent No.: US 6,573,280 B2
(45) Date of Patent: Jun. 3, 2003

(54) CALCIUM BLOCKERS TO TREAT PROLIFERATIVE VITREORETINOPATHY

(75) Inventor: Evan B. Dreyer, Pittsburgh, PA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/038,215

(22) Filed: Jan. 2, 2002

(65) Prior Publication Data

US 2003/0060510 A1 Mar. 27, 2003

Related U.S. Application Data

(63) Continuation of application No. 09/445,832, filed as application No. PCT/US98/12414 on Jun. 15, 1998, now Pat. No. 6,380,261.
(60) Provisional application No. 60/051,962, filed on Jun. 30, 1997.

(51) Int. Cl.$^7$ ............................................. A61K 31/445
(52) U.S. Cl. ........................ 514/317; 514/656; 514/912
(58) Field of Search ................................ 514/317, 656, 514/912

(56) References Cited

U.S. PATENT DOCUMENTS

| | | |
|---|---|---|
| 5,431,907 A | 7/1995 | Abelson et al. |
| 5,623,051 A | 4/1997 | Catterall et al. |
| 5,710,165 A * | 1/1998 | Kapin et al. ................. 514/317 |

OTHER PUBLICATIONS

Machamer (1978) British J. Ophthal. 62:737.
Hilton et al (1983) Ophthalmology 90:121.
Sommer et al , "Glutamate receptor channels: novel properties and new clones", Trends Pharmacological Sciences 13: 291–296 (1992).
Nakanishi, "Molecular Diversity of glutamate receptors and implications for brain function", Science 248: 597–603 (1992).
Karschian et al, J. Physiol. 418: 379–396 (1989).
Watkins et al, Trends in Pharmacological Sci. 11: 25, 1990.
Bean, Annual Rev. Physiol. 51: 367–384 (1989).
Hess, Annual Rev. Neurosci. 13:337–356 (1990).
Kiumura et al, Human Gene Therapy, 7: 799–808 (1996).
Sakamoto et al, Ophthalmology 102: 1417–1421 (1995).
Handa et al, Experimental Eye Research 62: 689–696 (1996).
Berger et al 37: 2318–2325 (1996).
de Souza et al, Ophthalmologica 209: 212–216 (1995).
Nakagawa et al, Ophthalmology & Visual Science 36: 2388–2395 (1995).
Steinhorst et al, Archive for Clinical & Experimental Ophthalmology 232: 347–354 (1994).

\* cited by examiner

*Primary Examiner*—Zohreh Fay
(74) *Attorney, Agent, or Firm*—Brent A. Johnson; Robert J. Baran; Martin A. Voet

(57) ABSTRACT

Glutamate causes migration and proliferation of retinal pigment epithelium and/or glial cells, and glutamate antagonists can prevent, treat or reduce retinal pigment epithelium and/or glial migration and the subsequent development of proliferative vitreoretinopathy. Avoidance or management of proliferative vitreoretinopathy can be achieved by administering to the patient a compound capable of reducing glutamate-induced retinal cell migration in a concentration effective to reduce such migration.

14 Claims, No Drawings

CALCIUM BLOCKERS TO TREAT PROLIFERATIVE VITREORETINOPATHY

CROSS REFERENCE TO RELATED PATENT APPLICATIONS

This patent application is a continuation of U.S. patent application Ser. No. 09/445,832 which was filed on Dec. 13, 1999 now U.S. Pat. No. 6,380,261 as the U.S. National Patent Application of PCT/US98/12414, which was filed on Jun. 15, 1998 and was based on U.S. Provisional Application No. 60/051,962, which was filed on Jun. 30, 1997 in the name of Dreyer.

BACKGROUND OF THE INVENTION

This application relates to preventing, controlling reducing and/or treating proliferative vitreoretinopathy. Proliferative vitreoretinopathy (including epiretinal membrane formation) is a potentially devastating ophthalmic condition that can lead to blindness. It can develop after any penetration of the eye—surgical or traumatic. Predisposing conditions therefore include, but are not limited to, penetrating trauma, retinal tears, traction detachments, vitrectomy, and intraocular surgery. Any ophthalmic condition that precipitates or permits migration of retinal pigment is epithelium or glial cells can lead to the development of proliferative vitreoretinopathy. See Machamer (1978) British J. Ophthal. 62:737; Hilton et al. (1983) Ophthalmology 90:121.

SUMMARY OF THE INVENTION

I have discovered that glutamate causes migration and proliferation of retinal pigment epithelium and/or glial cells. The invention features the use of glutamate antagonists to reduce or control retinal pigment epithelium and/or glial migration and the subsequent development of proliferative vitreoretinopathy. Avoidance or management of proliferative vitreoretinopathy can be achieved by administering to the patient a compound capable of reducing glutamate-induced retinal pigment epithelium and/or glial migration in a concentration effective to reduce such migration.

While I do not wish to be bound to any specific theory, I conclude that one or more of the several types of calcium-permeable CNS ion channels mentioned below can be involved in controlling such migration, including: a) the various aspects of the NMDA (N-methyl-D-aspartate) receptor channel complex; b) the voltage-dependent $Ca^{2+}$ channels; and c) other channels directly coupled to glutamate (or excitatory amino acid) receptors. Such channels are reviewed in: Sommer, B. and Seeburg, P. H. "Glutamate receptor channels: novel properties and new clones" *Trends Pharmacological Sciences* 13:291–296 (1992); Nakanishi, S., "Molecular Diversity of glutamate receptors and implications for brain function", *Science* 248:597–603 (1992).

One aspect of the invention generally features a method of treating, preventing, or reducing proliferative vitreoretinopathy in a patient by administering to the patient's retina an effective amount of a compound that reduces CNS neuronal damage incident to (associated with) calcium ion influx.

A second aspect of the invention features treating, preventing, or reducing proliferative vitreoretinopathy in a patient by administering to the patient's retina an effective amount of at least one of the compounds listed in one or more of Tables 2–5. below.

A third aspect of the invention features treating preventing or reducing proliferative vitreoretinopathy in a patient by administering to the patient's retina an effective amount of a compound that reduces glutamate related retinal cell migration, proliferation, or both.

The compound may be one of the so-called NMDA antagonists—i.e., it reduces neuronal damage mediated by the NMDA receptor complex. Alternatively, the compound antagonizes neuronal damage mediated by the voltage-dependent calcium channel. Other useful compounds are those which limit release of glutamate from cells or reduce the intracellular neurotoxic consequences of glutamate interaction with cell membrane glutamate receptors. Preferably, the compound crosses the blood-retinal barrier.

The patient may be anyone who has experienced, or is at risk for experiencing, penetrating trauma, retinal tear, traction detachment, vitrectomy, or intraocular surgery. The compound may be administered to the patient topically, orally, or intravitreally, as well as by other routes described below. It may be administered chronically, i.e., over an extended period of a month or even six months or years.

The invention preferably will be used to treat patients having proliferative vitreoretinopathy or to treat patients prophylactically to avoid that condition. Preferably, the agent is administered over an extended period (e.g., at least six months and preferably at least one year). Those at risk for developing proliferative vitreoretinopathy include patients who have experienced penetrating trauma, retinal tears, traction detachments, vitrectomy, or intraocular surgery.

Particularly preferred compounds are antagonists of the NMDA receptor-channel complex. The term "NMDA receptor antagonists" includes several sub-types of NMDA antagonists including: a) channel blockers—i.e., antagonists that operate uncompetitively to block the NMDA receptor channel; b) receptor antagonists—antagonists that compete with NMDA to act at the NMDA binding site; c) agents acting at either the glycine co-agonist site or any of several modulation sites such as the zinc site, the magnesium site, the redox modulatory site, or the polyamine site; d) agents which inhibit the downstream effects of NMDA receptor stimulation, such as agents that inhibit activation of protein kinase C activation by NMDA stimulation, antioxidants, and agents that decrease phosphatidylinositol metabolism.

Other compounds that are useful in the invention include voltage-dependent calcium channel antagonists, e.g. those which exert a substantial direct effect on glutamate toxicity mediated by the L-type voltage dependent Ca++ channel in that they produce a statistically significant result in experiments measuring glutamate induced effects by the general method described in Karschian and Lipton, *J. Physiol.* 418: 379–396 (1989) or by other techniques for measuring antagonism of the L-type Ca++ channel known to those in the art. (We contrast the direct effect so measured with the secondary effects of excitoxicity mediated by other channels, which in turn causes flow through the voltage dependent Ca++ channels.) Particular candidate compounds include Class I voltage dependent Ca++ channel antagonists, e.g., phenylalkylamines.

Preferably, the compounds used cross the blood-retina barrier and can be administered chronically. Other useful agents act as antagonists of non-NMDA receptors (glutamate receptor types other than the NMDA receptor complex discussed above), and include agents which block inotropic glutamate receptors or interact with metabotropic glutamate receptors (Nakanishi, supra). Still other agents act to limit (reduce) release of glutamate from cells, thereby acting upstream from the glutamate receptors in the excitatory neurotoxicity process. Still other agents may act by blocking downstream effects of glutamate receptor stimulation, e.g., the intracellular consequences of glutamate interaction with a cell membrane glutamate receptor, such as agents (like dantrolene) that block the rise in intracellular calcium following stimulation of membrane glutamate receptors.

The most preferred compounds are those capable of crossing the blood-retinal barrier; these compounds may be administered orally, intravenously, or topically and cross intervening barriers including the blood-retina barrier to reach the retinal ganglion cells. Compounds that do not freely cross the blood-retina barrier are less preferred; these compounds may be administered intravitreally to the retina. In the case of compounds that have an intermediate ability to cross the blood-retina barrier, the mode of administration will depend on the dosage required and other factors.

Among the preferred compounds are amantadine derivatives (e.g., memantine, amantadine, and rimantadine), nitroglycerin, dextorphan, dextromethorphan, and CGS-19755. See generally, the compounds listed in Table 2.

The invention is useful for the reduction or prevention (including prophylactic treatment) of damage as a result of proliferative vitreoretinopathy.

Other features and advantages of the invention will be apparent from the following description of the preferred embodiments thereof, and from the claims.

DESCRIPTION OF THE PREFERRED EMBODIMENTS

Selection of Antagonists

In view of our discovery that glutamate is associated with proliferative vitreoretinopathy, the invention features antagonists having certain specific characteristics: the ability to cross the blood-retina barrier; and the ability to be administered chronically. Within those guidelines, any suitable antagonist of the glutamate induced excitotoxicity may be used in accordance with the invention. As mentioned, in preferred embodiments, N-methyl-D-aspartate (NMDA) subtype of glutamate receptor-channel complex may be used to reduce or prevent proliferative vitreoretinopathy-related injury. Many antagonists of the NMDA receptor have been identified (Watkins et al., Trends in Pharmacological Sci. 11:25, 1990, hereby incorporated by reference). There are several recognized sub-types of NMDA receptor including: a) channel blockers—i.e., antagonists that operate non-competitively to block the NMDA receptor channel; b) receptor antagonists—antagonists that compete with NMDA, acting at the NMDA binding site; c) agents acting at either the glycine co-agonist site or any of several modulation sites such as the zinc site, the magnesium site, the redox modulatory site, or the polyamine site; d) agents which inhibit the downstream effects of NMDA receptor stimulation such as agents that inhibit activation of protein kinase C activation by NMDA stimulation, antioxidants, and agents that decrease phosphatidylinositol metabolism.

Other compounds that are useful in this invention include non-NMDA receptor antagonists, such as agents which block other types of inotropic glutamate receptors or interact with metabotropic glutamate receptors; voltage-dependent calcium channel antagonists (against L, N, T, and P type channels) (Bean, B. P. Annu. Rev. Physiol. 51:367–384 (1989); Hess, P. Annu. Rev. Neurosci. 13:337–356 (1990)), and are described in greater detail below; and agents which act to decrease the release of glutamate, thereby acting upstream in the excitatory neurotoxicity process.

Table 1, below, lists various suitable NMDA and non-NMDA receptors which do not operate via the voltage-dependent Ca++ ion channel. Tables 2–4 list antagonists of the voltage dependent Ca++ channel, which can be used by themselves in connection with the first aspect of the invention, and which can also be used in combination with other antagonists in the second aspect of the invention.

| NMDA Antagonists | NMDA Antagonists | NMDA Antagonists |
| --- | --- | --- |
| 1. Competitive NMDA Antagonists (act at agonist binding site) | 2. Channel Blockers (Un-Competitve NMDA Antagonists) | 3. Antagonists at Glydne Site of the NMDA Receptor |
| CGS-19755 (CIBA-GEIGY) and other piperdine derivatives, D-2-amino-5-phosphovalerate, D-2-amino-7-phosphosoheptanoate (AP7) | MK-801 (Dizocilpine) and other derivatives of dibenzyocycloheptene (Merck) | Kynurenate, 7-chloro-kynurenate, 5,7-chloro-kynurenate, thio-derivatives, and other derivatives. (Merck) |
| CPP {[3-2-carboxypiperazin-4-y-propyl-1-phosphonic acid]} | Sigma receptor ligands, e.g. Dextrorphan, dextromethorphan and morphiasn derivatives (Hoffman La Roche) such as caramiphen and rimcazole (which also block calcium channels) | Indole-2-carboxylic acid |
| LY 274614, CGP39551, CGP37849, LY233053, LY233536 | Ketamine, Tiletamine and other cyclohexanes | DNQX |
| O-phosphohomoserine | Phencyclidine (PCP) and derivatives, and pyrazine compounds | Quinoxaline or oxidiazole derivatives including CNQX, NBQX |
| MDL100,453 | Memantine, amantadine, rimantadine and derivatives | Glycine partial agonist (e.g. Hoecht-Roussel P-9939 |
|  | CNS 1102 (and related bi- and tri-substituted guanidines) |  |
|  | Diamines |  |
|  | Conantokan peptide from Conus geographus |  |
|  | Agatoxis-489 |  |
| 4. Polyamine Site of NMDA Receptor | 5. Redox Site of NMDA Receptor | 6. Other Non-Competitve NMDA Antagonists |
| Arcaine and relate biguanidines and biogenic polyamines | Oxidized and reduced glutathione | Hoechst 831917189 |
| Ifenprodil and related drugs | PQQ (pyrroloquinoline quinone) | SKB Carvedilol |
| Diethylenetriamine SL 82,0715 | Compounds that generate Nitric Oxide (NO) |  |

-continued

| | or other oxidation states of nitrogen monoxide (NO+, NO-) including those listed in the box below | |
|---|---|---|
| 1,10-diaminodecane (and related inverse agonists) | Nitroglycerin and derivatatives, Sodium Nitroprusside, and other NO generating listed on p.5 of this table<br>Nitric oxide synthase (NOS) Inhibitors:<br>Arginise analogs including N -mono-methyl-L-arginine (NMA);N -amino-L-argenine (NAA):N -nitro-L-arginine (NNA); N -nitro-L-arginine methyl ester; N-iminoethyl-L-ormithine<br>Flavin Inhibitors; diphenyliodinium;<br>Calmodulia inhibitors, trifluoperizine<br>Calcineurin Inhibitors, e.g., FK-506 (inhibits caleineurin and thus NOS diphosphorylase) | |

| Inhibitors of Downstream Effects of NMDA | Inhibitors of Downstream Effects of NMDA | Non-NMDA Receptor Antagonists |
|---|---|---|
| 7. Agents to inhibit protein kinase C activation by NMDA stimulation (Involved in NMDA toxicity)<br>MDL 27,266 (Merrill Dow) and triazole-one derivatices<br>Mososialoganglioxides (eg GMI of Fidin Corp.) and other ganglioside derivatives LIGA20, LIGA4 (may also effect calcium extrusion via calcium ATPase) | 8. Downstream effects from Receptor Activation<br><br>8a. To decrease phopshatidylinositol metabolism<br>kappa opioid receptor agonist: U50488(Upjohn) and dynorphan<br><br>kappa opioid receptor agonist: PD117302, CI-977<br><br>8b. To decrease hydrogen peroxide and free radical injury, eg antioxidants 21-aminosteroid (lazaroids) such as U74500A, U75412E and U74006F U74389F, FLE26749, Trolox (water soluble alpha tocophenol), 3,5-dialkoxy-4-hydroxy-benzylamines<br>Compounds that generate Nitric Oxide (NO) or other oxidation states of nitrogen monoxide (NO+, NO-) including those listed in the box below<br>Nitroglycerin and derivatives, Sodium Nitroprusside, and other NO generating listed on p. 5 of this table<br>Nitric oxide synthase (NOS) Inhibition:<br>Arginine analogs including N -mono-methyl-L-arginine (NMA): N -amino-L-arginine (NAA):N -nitro-L-arginine (NNA):N -nitro-L-arginine methyl ester; N-iminoethyl-L-omithine | 9A. Non-NMDA antagonists (Competitive)<br><br>CNQX, NBQX, YM900, DNQX. PD140532<br>AMOA (2-amino-3[3-9carboxymethoxyl-5-methoxylisoxazol-4-yl]propionate]<br><br>2-phosphophonoethyl phenylalanine derivatives, i.e. 5-ethyl, 5-methyl, 5-trifluoromethyl<br><br>9B. Non-NMDA Non competitve antagonists<br>GYK152466<br><br><br>Evans Blue |

| Agents Active at Metabotropic Glutamate Receptors | Decrease glutamate release | Drugs to derease intracellular calcium following glutamate receptor stimulation |
|---|---|---|
| 10a. Blockers of Metabotropic Glutamate Receptors<br>AP3 (2-amino-3-phosphonoprionic acid)<br><br>10b. Agonists of Metabotrpic Glutamate Receptors<br>(1S, 3R)-1-Amino-cyclopentane-1,3-dicarboxylic acid [(1S.3R)-ACPD], commonly ref as 'trans'-ACPD | 11. Agents to decrease glutamate release<br><br>Adenosine, and derivatives, e.g. cyclohexyladenosine<br>CN51145<br><br>Conopeptides: SNX-111, SNX-183, SNX-230<br><br>Omega-Aga-IVA, toxin from venom of funnel web spider<br>Compounds that generate Nitric Oxide (NO) or other oxidation states of nitrogen monoxide (NO+, NO-) including those listed in the box below<br>Nitroglyccerin, and derivatives, Sodium Nitroprusside, and other NO generating listed on p.5 of this table<br>Nitric oxide synthase (NOS) Inhibitors:<br>Arginine analogs including N -mono-methyl-L-arginine (NMA);N -amino-L-arginine (NAA): N nitro-L-arginine | 12a. Agents to decrease Intracellular calcium release<br>Dantrolene (sodium dantrium): Ryanodine (or ryanodine + caffiene<br>12b. Agents Inhibiting intracellular Calcium-ATPase<br>Thaprigargin, cyclopiazosic acid, BHQ ([2,5-di-(tert butyl)-1,4-benzohydroquinose; 2,5-di-(tert-butyl)-1,4benzohydroquinose]) |

-continued (NNA):N -nitro-L-arginine methyl ester,
N-iminoethyl-L-omithine
Additional NO-generating
compounds
Isosorbide
dinitrate (isordil)
S-nitrosocaptopril
(SnoCap)
Serum albumin coupled to
nitric oxide (SA-NO)
Cathepsin coupled to nitric
oxide (cathepsin-NO)
Tissue plasminogen
activator coupled to
NO (TPA-NO)
SIN-1 (also known as
SIN1 or molsidomine)
Ion-nitrosyl complees (e.g.,
nitrosyl-iron complexes,
with iron in the Fe2+ state)
Nicorandil

TABLE 2

Antagonists of the Voltage Dependent Calcium Channels (N, L. T, P and other types)

dihydropyridines (e.g., nimodipine)
phenylalkylamines (e.g., verapamil, (S)-emopamil, D-600, D-888)
benzothiazepines (e.g., diltiazem and others)
bepridil and related drugs
diphenylbutylpiperdines
diphenylpiperazines (e.g., flunarizine/cinnarizine series)
HOE 166 and related drugs
fluspirilene and related drugs
toxins and natural compounds (e.g., snail toxins -
(ωconotoxin GVIA and GVIIA, maitotoxin, taicatoxin,
tetrandine, hololena toxin, plectreurys toxin,
funnel-web spider venom and its toxin fraction,
agatoxins including ω-agatoxin IIIA and ω-agatoxin IVA.

TABLE 3

DIHYDROPYRIDINE CALCIUM CHANNEL ANTAGONISTS

| nifedipine | KW3049 |
| niludipine | oxodipine |
| PY108-068 (darodipine) | CD349 |
| mesudipine | TC81 |
| GX 1048 | YM-09730-5 or (4S)DHP |
| floridine | MDL72567 |
| nitrendipine | Ro18-3981 |
| nisoldipine | DHP-218 |
| nimodipine | nilvadipine |
| nicardipine | amlodipine |
| felodipine | 8363-S |
| PN200-110 (Isradipine) | iodipine |
| CV4093 | azidopine |

TABLE 4

OTHER CALCIUM CHANNEL ANTAGONISTS

| diclofurime | D-600 |
| pimozide | D-888 |
| prenylamine | Smith Kline 9512 |
| fendiline | ranolzine |
| perhexiline | lidoflazine |

TABLE 4-continued

OTHER CALCIUM CHANNEL ANTAGONISTS

| mioflazine | CERM-11956 |
| flunarizine/cinnarizine series | R-58735 |
| | R-56865 |
| verapamil | amiloride |
| dilfiazine | phenytoin |
| dipropervine | thioridazine |
| (S)-emopamil | tricyclic antidepressents |

In Vitro Assay

An antagonist may be tested for utility in the method of the invention by monitoring its effect on proliferative retinopathy as follows.

Cultured fibroblasts will be injected into the vitreous of the rabbit eye. After two weeks, the degree of vitreopathy can be assessed histologically. At the time of the initial insult, the animals will be treated with the compound under consideration.

Such models are well known. A few examples (hereby incorporated by reference) included Kiumura et al. *Human Gene Therapy*, 7:799–808 (1996); Sakamoto et al., *Ophthalmology* 102:1417–1421 (1995); Handa et al. *Experimental Eye Research* 62:689–696 (1996); Berger et al. 37: 2318–1325 (1996); de Souza et al. *Ophthalmologica* 209: 212–216 (1995); Nakagawa et al. *Ophthalmology & Visual Science* 36:2388–2395 (1995); Steinhorst et al. *Archive for Clinical & Experimental Ophthalmology* 232:347–354 (1994).

Use

An effective receptor antagonist will cause a decrease in proliferative vitreoretinopathy. As described above, the preferred compounds which cross the blood-retinal barriers are preferably administered topically or orally in known, physiologically acceptable vehicles including tablets, liquid excipients and suspensions. Those skilled in the art will appreciate how to formulate acceptable therapeutics.

Antagonists may be compounded into a pharmaceutical preparation, using pharmaceutical compounds well-known in the art; the exact formulation and dosage of the antagonist compound depends upon the route of administration.

Generally, the effective daily dose of the antagonists will range from 0.01 to 1000 mg/kg.

OTHER EMBODIMENTS

Other embodiments are within the following claims. In the method of the invention, a useful compound may be administered by any means that allows the compound access to the retina. The compounds useful in the method include antagonists of excitatory amino acid receptors (both NMDA and non-NMDA subtypes) that act to reduce retinal cell migration or proliferation or reduce binding of glutamate to the NMDA receptor. The antagonists can act at a modulatory site or a co-agonist site or by blocking the chain of events initiated by receptor activation.

Other embodiments are within the following claims.

What is claimed is:

1. A method of treating or reducing proliferative vitreoretinopathy in a patient by administering to the patient's retina an effective amount of a glutamate agonist that reduces CNS neuronal damage incident to calcium ion influx.

2. A method of treating proliferative vitreoretinopathy in a patient by administering to the patient's retina an effective amount of a glutamate agonist that reduces glutamate related retinal cell migration, proliferation, or both.

3. The method of claim 1 or 2 in which the compound inhibits glutamate-related proliferation of retinal cells.

4. The method of claim 1 or 2 in which the compound inhibits glutamate-related migration of retinal cells.

5. The method of claim 1 or 2 in which the compound controls the NMDA receptor complex-mediated activity.

6. The method of claim 1 or 2 in which the compound controls the voltage-dependent calcium channel activity.

7. The method of claim 1 or 2 in which the compound crosses the blood-retinal barrier.

8. The method of claim 1 or 2 in which the 5 patient has or will experience penetrating trauma, retinal tear, traction detachment, vitrectomy, or intraocular surgery.

9. The method of claim 1 or 2, said compound being administered to said patient topically.

10. The method of claim 1 or 2, said compound being administered to said patient orally.

11. The method of claim 1 or 2, said compound being administered to said patient intravitreally.

12. The method of claim 1 wherein said compound is administered chronically.

13. The method of claim 1 or 2 wherein said compound limits release of glutamate from cells.

14. The method of claim 1 or 2, wherein said compound controls glutamate interaction with cell membrane glutamate receptors.

* * * * *

UNITED STATES PATENT AND TRADEMARK OFFICE
CERTIFICATE OF CORRECTION

PATENT NO. : 6,573,280 B2  Page 1 of 1
DATED : June 3, 2003
INVENTOR(S) : Dreyer It is certified that error appears in the above-identified patent and that said Letters Patent is hereby corrected as shown below:

Column 9,
Line 20, the word "agonist" should read -- antagonist --.
Line 25, the word "agonist" should read -- antagonist --.

Signed and Sealed this

Twenty-eighth Day of October, 2003

JAMES E. ROGAN
*Director of the United States Patent and Trademark Office*